United States Patent
Genet et al.

(10) Patent No.: US 6,270,533 B1
(45) Date of Patent: Aug. 7, 2001

(54) CATIONIC OXIDATION BASES, THEIR USE FOR OXIDATION DYEING OF KERATIN FIBRES, DYEING COMPOSITIONS AND DYEING METHODS

(75) Inventors: Alain Genet, Aulay-sous-Bois; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/254,664

(22) PCT Filed: Jul. 13, 1998

(86) PCT No.: PCT/FR98/01536

§ 371 Date: Jun. 7, 1999

§ 102(e) Date: Jun. 7, 1999

(87) PCT Pub. No.: WO99/03834

PCT Pub. Date: Jan. 28, 1999

(30) Foreign Application Priority Data

Jul. 16, 1997 (FR) .................................................. 97/09029

(51) Int. Cl.$^7$ .......................... C09B 69/02; C09B 69/32; C09B 67/00; A61K 7/13; A45D 19/00; C07D 233/54; C07D 521/00

(52) U.S. Cl. .......................... 8/406; 8/407; 8/408; 8/409; 8/410; 8/416; 8/655; 8/421; 8/423; 8/426; 8/573; 8/606; 8/654; 564/282; 564/290; 548/314.4; 548/335.5; 548/346.1

(58) Field of Search .............................. 8/406, 407, 408, 8/409, 410, 416, 421, 423, 426, 573, 606, 654, 655; 564/282, 290; 548/314.4, 335.5, 346.1

(56) References Cited

U.S. PATENT DOCUMENTS

| | | | |
|---|---|---|---|
| 3,100,739 | 8/1963 | Kaiser et al. ............................. | 8/426 |
| 3,442,895 | 5/1969 | Bugaut et al. ......................... | 544/156 |
| 3,467,483 | 9/1969 | Bugaut et al. ............................. | 8/426 |
| 3,528,972 | 9/1970 | Kalopissis et al. .................... | 544/156 |
| 3,622,629 | * 11/1971 | Lugosy et al. ........................ | 564/287 |
| 4,581,370 | * 4/1986 | Diamond et al. .................. | 548/335.5 |
| 4,888,025 | * 12/1989 | Bugaut et al. ............................. | 8/405 |
| 4,975,092 | 12/1990 | Chan et al. ............................... | 8/408 |
| 5,135,543 | 8/1992 | Chan et al. ............................... | 8/405 |
| 5,137,538 | 8/1992 | Madrange et al. ...................... | 8/410 |
| 5,139,532 | 8/1992 | Chan et al. ............................... | 8/405 |
| 5,344,464 | 9/1994 | Madrange et al. ...................... | 8/410 |
| 5,514,188 | 5/1996 | Cotteret et al. .......................... | 8/412 |
| 5,735,908 | 4/1998 | Cotteret et al. .......................... | 8/410 |
| 5,735,910 | 4/1998 | Lagrange et al. ........................ | 8/415 |
| 6,024,768 | * 2/2000 | Bittner et al. ............................ | 8/410 |

FOREIGN PATENT DOCUMENTS

| | | |
|---|---|---|
| 616 439 | 10/1962 | (BE) . |
| 1 135 589 | 8/1962 | (DE) . |
| 1 292 784 | 4/1969 | (DE) . |
| 0 360 644 | 3/1990 | (EP) . |
| 0 544 400 | 6/1993 | (EP) . |
| 0 634 164 | 1/1995 | (EP) . |
| 0 673 641 | 9/1995 | (EP) . |
| 0 673 926 | 9/1995 | (EP) . |
| 0 728 463 | 8/1996 | (EP) . |
| 1 391 675 | 12/1965 | (FR) . |
| 2 213 968 | 8/1974 | (FR) . |
| 2 217 390 | 9/1974 | (FR) . |
| 2 586 913 | 3/1987 | (FR) . |
| 2 630 438 | 10/1989 | (FR) . |
| 1 211 801 | 11/1970 | (GB) . |
| 1 364 952 | 8/1974 | (GB) . |
| 2 018 453 | 10/1979 | (GB) . |
| WO 95/01772 | 1/1995 | (WO) . |
| WO 95/12585 | 5/1995 | (WO) . |
| WO 95/15144 | 6/1995 | (WO) . |
| WO 97/39727 | 10/1997 | (WO) . |
| 98/01418 | * 1/1998 | (WO) . |

OTHER PUBLICATIONS

L.K.J. Tong et al., "The Mechanism of Dye Formation in Color Photography. VII. Intermediate Bases in the Deamination of Quinonediimines", Journal of American Chemical Scoeity, vol. 82, No. 8, Apr. 1960, pp. 1988–1996.
English language Derwent Abstract of EP 0 728 463, 8/96.
English language Derwent Abstract of FR 2 213 968, 9/74.
English language Derwent Abstract of FR 2 217 390, 10/74.
English language Derwent Abstract of FR 2 586 924, 3/87.
English language Derwent Abstract of FR 2 630 438, 10/89.
C. Tomaier, "Phenols, Anilines: Bases Coupleurs a Azote Quaternaire Extra–Nucleaire", Bibliographie No. 307, Jun. 1996, pp. 2–28.
C. Tomaier, "Bis–Quaternaires en Cosmetique", Bibliographie No. 317, Feb. 1997, pp. 2–35.
Olovyanishnikova, Z.A. et al., Chemical Abstracts, vol. 109, No. 19, 109:170317v, Nov. 7, 1988.

* cited by examiner

Primary Examiner—Margaret Einsmann
(74) Attorney, Agent, or Firm—Finnegan, Henderson, Farabow, Garrett & Dunner, L.L.P.

(57) ABSTRACT

The invention relates to novel dibenzene oxidation bases containing at least one cationic group Z, Z being chosen from quaternized aliphatic chains, aliphatic chains containing at least one quaternized saturated ring and aliphatic chains containing at least one quaternized unsaturated ring, to their use for the oxidation dyeing of keratin fibres, to dye compositions containing them and to oxidation dyeing processes using them.

39 Claims, No Drawings

CATIONIC OXIDATION BASES, THEIR USE FOR OXIDATION DYEING OF KERATIN FIBRES, DYEING COMPOSITIONS AND DYEING METHODS

The invention relates to novel dibenzene oxidation bases containing at least one cationic group Z, Z being chosen from quaternized aliphatic chains, aliphatic chains containing at least one quaternized saturated ring and aliphatic chains containing at least one quaternized unsaturated ring, to their use for the oxidation dyeing of keratin fibres, to dye compositions containing them and to oxidation dyeing processes using them.

It is known practice to dye keratin fibres, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

It has already been proposed, in particular in U.S. Pat. No. 5,139,532, to use certain cationic para-phenylenediamine derivatives, i.e. more precisely, para-phenylenediamines in which one of the amino groups is monosubstituted with a quaternized aliphatic chain, for the oxidation dyeing of keratin fibres in strong shades which are redder than those usually obtained using standard para-phenylenediamines, i.e. compounds containing no cationic groups. However, the use of the para-phenylenediamines described in that prior patent does not make it possible to obtain a wide range of colours and, furthermore, the colorations obtained are not always entirely satisfactory from the point of view of their resistance with respect to the various forms of attack to which the hair may be subjected (action of light, perspiration, shampoo, etc.).

Now, the Applicant has just discovered, entirely surprisingly and unexpectedly, that certain novel dibenzene oxidation bases of formula (I) defined below, containing at least one cationic group Z, Z being chosen from quaternized aliphatic chains, aliphatic chains containing at least one quaternized saturated ring and aliphatic chains containing at least one quaternized unsaturated ring, are not only suitable for use as oxidation dye precursors, but also allow dye compositions to be obtained which lead to strong colorations, in a wide range of colours, and which have excellent properties of resistance to the various treatments to which keratin fibres may be subjected. Lastly, these compositions prove to be readily synthesizable.

These discoveries form the basis of the present invention.

A first subject of the invention is thus novel compounds of formula (I) below, and the addition salts thereof with an acid:

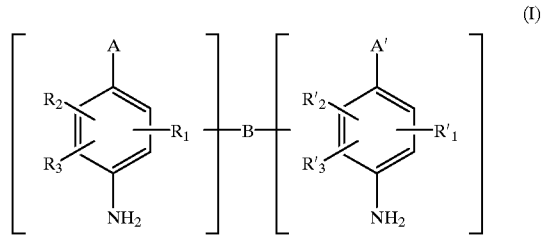

in which:

B is a linker arm which represents a group Z or an alkyl chain preferably containing from 1 to 14 linear or branched carbon atoms which can be interrupted by one or more groups Z and/or by one or more hetero atoms such as oxygen, sulphur or nitrogen atoms, and optionally substituted with one or more hydroxyl or $C_1$–$C_6$ alkoxy radicals, and possibly bearing one or more ketone functions;

$R_1$, $R_2$, $R_3$, $R'_1$, $R'_2$ and $R'_3$, which may be identical or different, represent a linker arm B, a hydrogen atom; a halogen atom; a group Z; a ($C_1$–$C_6$)alkylcarbonyl radical; an amino($C_1$–$C_6$)alkylcarbonyl radical; an N-Z-amino($C_1$–$C_6$)alkylcarbonyl radical; an N-($C_1$–$C_6$) alkylamino($C_1$–$C_6$)alkylcarbonyl radical; an N,N-di ($C_1$–$C_6$)alkylamino($C_1$–$C_6$)alkylcarbonyl radical; an amino-($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N-Z-aminosulphonyl radical; a $C_1$–$C_6$ N-alkylaminosulphonyl radical; an N,N-di($C_1$–$C_6$) alkylaminosulphonyl radical; a $C_1$–$C_6$ aminosulphonylalkyl radical; a $C_1$–$C_6$ N-Z-aminosulphonylalkyl radical; an N-($C_1$–$C_6$)alkylaminosulphonyl($C_1$–$C_6$)alkyl radical; an N,N-di($C_1$–$C_6$)alkylaminosulphonyl ($C_1$–$C_6$)alkyl radical; a carbamyl radical; an N-($C_1$–$C_6$) alkylcarbamyl radical; an N,N-di($C_1$–$C_6$) alkylcarbamyl radical; a carbamyl($C_1$–$C_6$)alkyl radical; an N-($C_1$–$C_6$)alkylcarbamyl ($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a group $OR_6$ or $SR_6$; or an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$)alkylcarbonyl, N-Z-amino ($C_1$–$C_6$) alkylcarbonyl, N-($C_1$–$C_6$)alkylamino ($C_1$–$C_6$) alkylcarbonyl, N,N-di($C_1$–$C_6$)alkylamin6 ($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, $C_1$–$C_6$ alkylsulphonyl, aminosulphonyl, N-Z-aminosulphonyl, $C_1$–$C_6$ N-alkylaminosulphonyl, N,N-di($C_1$–$C_6$) alkylaminosulphonyl, thiocarbamyl or formyl radical, or with a group Z;

$R_6$ denotes a linker arm B, a $C_1$–$C_6$ alkyl radical; a $C_1$–$C_6$ monohydroxyalkyl radical; a $C_2$–$C_6$ polyhydroxyalkyl radical; a group Z; a (($C_1$–$C_6$)alkoxy($C_1$–$C_6$)alkyl radical; an aryl radical; a benzyl radical; a carboxy($C_1$–$C_6$) alkyl radical; a ($C_1$–$C_6$)alkylcarboxy($C_1$–$C_6$)alkyl radical; a cyano($C_1$–$C_6$)alkyl radical; a carbamyl($C_1$–$C_6$) alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$) alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro($C_1$–$C_6$)alkylcarbonyl, ($C_1$–$C_6$)alkylcarboxyl, carbamyl, N-($C_1$–$C_6$) alkylcarbamyl, N,N-di($C_1$–$C_6$)alkylcarbamyl, thiocarbamyl and $C_1$–$C_6$ alkylsulphonyl radicals, or with a group Z;

A represents a group —$NR_4R_5$ or a hydroxyl radical;

A' represents a group —$NR'_4R'_5$ or a hydroxyl radical;

$R_4$, $R_5$, $R'_4$ and $R'_5$, which may be identical or different, represent a linker arm B, a hydrogen atom; a group Z; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; an aryl radical; a benzyl radical; a cyano($C_1$–$C_6$)alkyl radical; a carbamyl ($C_1$–$C_6$)alkyl radical; an N-($C_1$–$C_6$)alkylcarbamyl ($C_1$–$C_6$)alkyl radical; an N,N-di($C_1$–$C_6$)alkylcarbamyl ($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from alkyl, $C_1$–$C_6$ monohydroxyalkyl, $C_2$–$C_6$ polyhydroxyalkyl, ($C_1$–$C_6$) alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$) alkylcarboxyl and thiocarbamyl radicals, or with a group Z;

Z is chosen from the unsaturated cationic groups of formulae (II) and (III) below, and the saturated cationic groups of formula (IV) below:

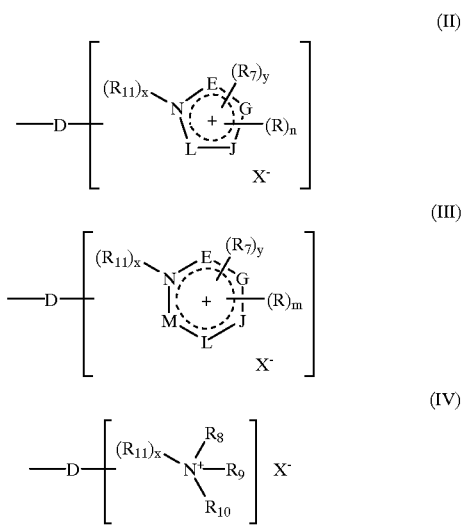

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1$–$C_6$ alkoxy radicals, and which can bear one or more ketone functions;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals R, which may be identical or different, represent a linker arm B, a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$) alkyl radical, a $C_1$–$C_6$ alkoxy radical, a tri($C_1$–$C_6$) alkylsilane($C_1$–$C_6$)alkyl radical, an amido radical, an aldehydo radical, a carboxyl radical, a ($C_1$–$C_6$) alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical; a group NHR" or NR"R'" in which R" and R'", which may be identical or different, represent a $C_1$–$C_6$ alkyl radical, a $C_1$–$C_6$ monohydroxyalkyl radical or a $C_2$–$C_6$ polyhydroxyalkyl radical;

$R_7$ represents a linker arm B, a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri ($C_1$–$C_6$)alkylsilane($C_1$–$C_6$)alkyl radical, a ($C_1$–$C_6$) alkoxy($C_1$–$C_6$)alkyl radical, a carbamyl($C_1$–$C_6$)alkyl radical, a ($C_1$–$C_6$)alkylcarboxy($C_1$–$C_6$)alkyl radical, a benzyl radical or a group Z of formula (II), (III) or (IV) as defined above;

$R_8$, $R_9$ and $R_{10}$, which may be identical or different, represent a linker arm B, a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy ($C_1$–$C_6$)alkyl radical, a cyano ($C_1$–$C_6$)alkyl radical, an aryl radical, a benzyl radical, a $C_1$–$C_6$ amidoalkyl radical, a tri($C_1$–$C_6$)alkylsilane ($C_1$–$C_6$)alkyl radical or a $C_1$–$C_6$ aminoalkyl radical in which the amine is protected with a ($C_1$–$C_6$) alkylcarbonyl, carbamyl or $C_1$–$C_6$ alkylsulphonyl radical; two of the radicals $R_8$, $R_9$ and $R_{10}$ can together also form, with the nitrogen atom to which they are attached, a saturated 5- or 6-membered carbon ring or a ring containing one or more hetero atoms such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$) alkylcarbonyl, carbamyl or $C_1$–$C_6$ alkylsulphonyl radical;

one of the radicals $R_8$, $R_9$ and $R_{10}$ can also represent a second group Z which is identical to or different from the first group Z;

$R_{11}$ represents a linker arm B, a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$) alkylcarbonyl, carbamyl or $C_1$–$C_6$ alkylsulphonyl radical; a carboxy($C_1$–$C_6$)alkyl radical; a cyano($C_1$–$C_6$) alkyl radical; a carbamyl($C_1$–$C_6$)alkyl radical; a $C_1$–$C_6$ trifluoroalkyl radical; a tri($C_1$–$C_6$)alkylsilane($C_1$–$C_6$) alkyl radical; a $C_1$–$C_6$ sulphonamidoalkyl radical; a ($C_1$–$C_6$)alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$) alkylcarbamyl($C_1$–$C_6$)alkyl radical; an N-($C_1$–$C_6$) alkylsulphonamido ($C_1$–$C_6$)alkyl radical;

x and y are integers equal to 0 or 1; with the following conditions:
in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_7$ is borne by the nitrogen atom of the unsaturated ring; or alternatively
2) when at least one of the ring members E, G, J and L represents a nitrogen atom to which the radical $R_7$ is attached;
in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M represents a divalent atom and when the radical $R_7$ is borne by the nitrogen atom of the unsaturated ring;
in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of the said saturated ring;

$X^-$ represents a monovalent or divalent anion and is preferably chosen from a halogen atom such as chlorine, bromine, fluorine or iodine, a hydroxide, a hydrogenosulphate or a $C_1$–$C_6$ alkyl sulphate such as, for example, a methyl sulphate or an ethyl sulphate; it being understood:
that the number of cationic groups Z is at least equal to 1;
that when A or A' represents a group —$NR_4R_5$ or —$NR'_4R'_5$, in which $R_4$ or $R_5$ or $R'_4$ or $R'_5$ represents a group Z in which the linker arm D represents an alkyl chain containing a ketone function, then the said ketone function is not directly attached to the nitrogen atom of the group —$NR_4R_5$ or —$NR'_4R'_5$;
that when A or A' represents a group —$NR_4R_5$ or —$NR'_4R'_5$ in which $R_4$ or $R_5$ or $R'_4$ or $R'_5$ represents a linker arm B defined as an alkyl chain containing a ketone function, then the said ketone function is not directly attached to the nitrogen atom of the group —$NR_4R_5$.

As mentioned above, the colorations obtained with the oxidation dye composition in accordance with the invention are strong and produce a wide range of colours. They moreover have excellent properties of resistance to the action of various external agents (light, bad weather, washing, permanent-waving, perspiration, friction). These properties are particularly noteworthy, in particular as regards the resistance of the colorations obtained to the action of light, washing, permanent-waving and perspiration.

In formula (I) above, the alkyl and alkoxy radicals can be linear or branched.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

Among the compounds of formula (I) above, mention may be made in particular of:

1,3-bis{3-{3'-[(4"-amino-3"-methylanilino)-N-propyl]}-3H-imidazol-1-ium}propane dichloride;

1,3-bis{3-{3'-[(4"-amino-2"-methylanilino)-N-propyl]}-3H-imidazol-1-ium}propane dichloride monohydrate diethanol;

1,3-bis{3-{3'-[(4"-aminoanilino)-N-propyl]}-3H-imidazol-1-ium}propane dichloride monohydrate ethanol;

1,3-bis{3-{3'-[(4"-aminoanilino)-N-propyl]}-3H-imidazol-1-ium}-2-propanol dichloride monohydrate;

$N_1,N_3$-bis[3-N-(4'-aminoanilino)propyl]-1,1,3,3-tetramethyldiammonium 1-3 propane dibromide monohydrate;

1,4-bis{3-[3-(2,5-diaminophenoxy)propyl]-3H-imidazol-1-ium}butane dichloride dihydrate;

1,3-bis[3-(2,5-diaminophenoxy)propyl]-3H-imidazol-1-ium monochloride monohydrate;

$N_1,N_4$-bis[3-N-methyl-N-(4'-aminoanilino)ethyl]-1,1,4,4-tetramethyldiammonium 1-3-propane dibromide monohydrate;

1,4-bis[3-(5-amino-2-hydroxybenzyl)-3H-imidazol-1-ium]butane dichloride monohydrate;

1,3-bis{[2-(4-aminoanilino)propyl]-1,1,3,3-tetramethyldiammoniumpropane dibromide;
1,3-bis{[4-(4-aminoanilino)pentyl]-1,1,3,3-tetramethyldiammonium}propane dichloride;
[4-(4-aminophenylamino)pentyl]-(5-amino-2-hydroxybenzyl)diethylammonium monochloride;
[2-(4-aminophenylamino)propyl]-(5-amino-2-hydroxybenzyl)dimethylammonium monochloride;
1,3-bis{3-[3-(2,5-diaminophenoxy)propyl]-3H-imidazol-1-ium}propane dichloride dihydrate;
1,3-bis(3-{3'-[(4"-aminoanilino)-N-propyl]}-3H-imidazol-1-ium}propane dichloride;
1,3-bis{4'-(4-[3-(4'-aminophenylamino)propyl]}-1,3-dimethyl-3H-imidazol-1-ium}propane dichloride,
1,3-bis{4'-(4-[3-(4"-amino-2"-methylanilino)propyl]-1,3-dimethyl-3H-imidazol-1-ium}propane dichloride;
4-[2-(2,5-diaminophenoxy)ethyl]-3-[3-(2,5-diaminophenoxy)propyl]-1-methyl-3-imidazol-1-ium monochloride;
4-[2-(2,5-diaminophenoxy)ethyl]-[3-(2,5-diaminophenoxy)propyl]-3-methyl-3-imidazol-1-ium monochloride;
and the addition salts thereof with an acid.

Among these compounds of formula (I), the ones more particularly preferred are:
1,3-bis{3-{3'-[(4"-aminoanilino)-N-propyl]}-3H-imidazol-1-ium}propane dichloride monohydrate ethanol;
1,3-bis[3-(2,5-diaminophenoxy)propyl]-3H-imidazol-1-ium monochloride monohydrate;
$N_1,N_4$-bis[3-N-methyl-N-(4'-aminoanilino)ethyl]-1,1,4,4-tetramethyldiammonium 1-3-propane dibromide monohydrate;
1,4-bis[3-(5-amino-2-hydroxybenzyl)-3H-imidazol-1-ium]butane dichloride monohydrate;
1,3-bis{3-{3'-[(4"-aminoanilino)-N-propyl]}-3H-imidazol-1-ium}propane dichloride;
and the addition salts thereof with an acid.

The compounds of formula (I) in accordance with the invention can be readily obtained according to methods that are well known in the state of the art:
either by reduction of the corresponding cationic dibenzene nitro compounds (cationic para-nitroanilinos and/or cationic para-nitrophenols),
or by reduction of the corresponding cationic nitroso compounds (obtained, for example, by nitrosation of a corresponding tertiary aniline or of a corresponding phenol),
or by reduction of the corresponding cationic azo compounds (reductive cleavage).

This reduction step (production of a primary aromatic amine) which gives the synthesized compound its nature as an oxidizable compound (oxidation base), which may or may not be followed by a salification, is generally, for convenience, the final step of the synthesis.

This reduction can take place earlier in the sequence of reactions leading to the preparation of the compounds of formula (I), and according to well-known processes it is then necessary to "protect" the primary amine created (for example by an acetylation, benzenesulphonation, etc. step), then carry out the desired substitution(s) or modification(s) (including quaternization) and end by "deprotecting" (generally in acidic medium) the amine function.

Similarly, the phenolic function can be protected according to well-known processes with a benzyl radical ("deprotection" by catalytic reduction) or with an acetyl or mesyl radical ("deprotection" in acidic medium).

When the synthesis is complete, the compounds of formula (I) in accordance with the invention can, if necessary, be recovered by methods which are well known in the state of the art, such as crystallization or distillation.

Another subject of the invention is the use of the compounds of formula (I) in accordance with the invention as oxidation bases for the oxidation dyeing of keratin fibres, and in of particular human fibres such as the hair.

The invention also relates to a composition for the oxidation dyeing of keratin fibres, and in particular of human keratin fibres such as the hair, characterized in that it comprises, as an oxidation base, in a medium which is suitable for dyeing, at least one compound of formula (I) in accordance with the invention.

The compound(s) of formula (I) in accordance with the invention preferably represent(s) from 0.0005 to 12% by weight approximately relative to the total weight of the dye composition, and even more preferably from 0.005 to 6% by weight approximately relative to this weight.

The medium which is suitable for dyeing (or the support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

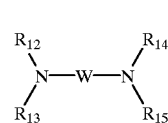

(V)

in which W is a propylene residue optionally substituted with a hydroxyl group or a $C_1$–$C_6$ alkyl radical; $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

The dye composition in accordance with the invention can also contain, in addition to the dyes defined above, at least one additional oxidation base which can be chosen from the oxidation bases conventionally used in oxidation dyeing and among which mention may be made in particular of para-phenylenediamines, bis(phenyl)alkylenediamines other than the compounds of formula (I) in accordance with the invention, para-aminophenols, ortho-aminophenols and heterocyclic bases.

Among the para-phenylenediamines which can be mentioned more particularly, for example, are para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline and the para-phenylenediamines described in French patent application FR 2,630,438, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)-ethylenediamine, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

When they are used, these additional oxidation bases preferably represent from 0.0005 to 12% by weight approximately relative to the total weight of the dye composition, and even more preferably from 0.005 to 6% by weight approximately relative to this weight.

The oxidation dye compositions in accordance with the invention can also contain at least one coupler and/or at least one direct dye, in particular in order to modify the shades or to enrich them with glints.

The couplers which can be used in the oxidation dye compositions in accordance with the invention can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers. preferably represent from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913 in the name of the Applicant.

The examples which follow are intended to illustrate the invention without, however, limiting its scope.

PREPARATION EXAMPLES

Preparation Example 1

Synthesis of 1,3-bis{3-{3'-[(4"-amino-3n-methylanilino)-N-propyl]}-3H-imidazol-1-ium}propane dichloride tetrahydrochloride 1/3 ethanol monohydrate

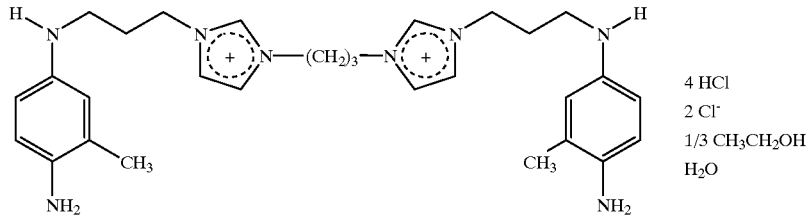

a) Preparation of (3-imidazol-1-ylpropyl)-(3-methyl-4-nitrophenyl)amine

A mixture of 125.5 g (1 mol) of 3-imidazol-1-ylpropylamine and 41.4 g (0.3 mol) of potassium carbonate in 140 ml of water was heated to 90° C. 77.6 g (0.5 mol) of 4-fluoro-2-methyl-1-nitrobehzene were added dropwise over45 minutes and the mixture was maintained at a temperature of 90–95° C. for 2 hours. The reaction mixture was cooled in an ice bath and the crystalline precipitate was filtered off, washed with water and dried at 40° C. under vacuum over phosphorus pentoxide.

After recrystallization from refluxing absolute ethanol, 96 g of yellow crystals melting at 133° C. (Kofler) were obtained, the elemental analysis of which, calculated for $C_{13}H_{16}N_4O_2$, was:

| % | C | H | N | O |
|---|---|---|---|---|
| calculated | 59.99 | 6.20 | 21.52 | 12.29 |
| found | 59.55 | 6.22 | 21.43 | 12.88 | b) Quaternization of (3-imidazol-1-ylpropyl)-(3-methyl-4-nitrophenyl)amine

A mixture of 88.9 g (0.341 mol) of (3-imidazol-1-ylpropyl)-(3-methyl-4-nitrophenyl)amine obtained in the previous step and 19.3 g (0.1705 mol) of 1,3-dichloropropane in 220 ml of normal pentanol was refluxed for 6 hours.

The reaction medium was a solution, which was cooled in an ice bath. A gum precipitated out and then recrystallized in bulk. This crude product was filtered off, washed with absolute ethanol, recrystallized from refluxing 95° ethanol and dried at 40° C. under vacuum. 56 g of yellow crystals of the expected product melting at 138–140° C. (Kofler) were obtained, the elemental analysis of which, calculated for $C_{29}H_{38}N_8O_4Cl_2 \cdot H_2O$, was:

| % | C | H | N | O | Cl |
|---|---|---|---|---|---|
| calculated | 53.46 | 6.19 | 17.20 | 12.28 | 10.88 |
| found | 52.69 | 6.25 | 17.06 | 12.89 | 10.99 | c) Preparation of 1,3-bis{3-{3'-[(4"-amino-3"methylanilino)-N-propyl]}-3H-imidazol-1-ium}propane dichloride tetrahydrochloride 43 g (0.068 mol) of the product obtained above in the previous step, 2 g of 5% palladium on charcoal (containing 50% water) and 170 ml of water were placed in a hydrogenator.

The reduction took place over one hour under a hydrogen pressure of about 5 bar and at a temperature which was gradually raised to 75° C.

After filtering off the catalyst under nitrogen, the filtrate was poured onto aqueous hydrochloric acid.

The filtrate was evaporated to dryness under reduced pressure and the partially crystalline compound was taken up in absolute ethanol until crystallization was complete.

After drying at 40° C. under vacuum and over potassium hydroxide, 38.4 g of white crystals melting with decomposition at 146–160° C. (Kofler) were obtained, the elemental analysis of which, calculated for $C_{29}H_{46}N_8Cl_6 \cdot H_2O \cdot 1/3CH_3CH_2OH$, was:

| % | C | H | N | O | Cl |
|---|---|---|---|---|---|
| calculated | 47.33 | 6.69 | 14.88 | 2.83 | 28.26 |
| found | 48.10 | 6.74 | 14.69 | 2.86 | 27.99 |

Preparation Example 2

Synthesis of 1,3-bis{3-{3'-[(4"-amino-2"-methylanilino)-N-propyl]}-3H-imidazol-1-ium}-propane dichloride tetrahydrochloride monohydrate diethanol

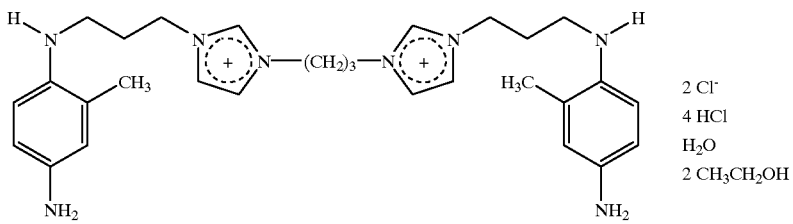

a) Preparation of (3-imidazol-1-ylpropyl)-(2-methyl-4-nitrophenyl)amine

A mixture of 250.4 g (2 mol) of 3-imidazol-1-ylpropylamine and 82.8 g (0.6 mol) of potassium carbonate in 280 ml of water was heated to 90° C. 155.1 g (1 mol) of 1-fluoro-2-methyl-4-nitrobenzene were added dropwise over 30 minutes and the mixture was maintained at a temperature of 90–95° C. for 4 hours.

The reaction mixture was cooled in an ice bath and the crystalline precipitate was filtered off, washed with isopropanol and dried at 40° C. under vacuum.

After recrystallization from refluxing 96° ethanol, 144.8 g of orange-coloured crystals melting at 163° C. (Kofler) were obtained, the elemental analysis of which, calculated for $C_{13}H_{16}N_4O_2$, was:

| % | C | H | N | O |
|---|---|---|---|---|
| calculated | 59.99 | 6.20 | 21.52 | 12.29 |
| found | 59.60 | 6.15 | 21.46 | 13.12 | b) Quaternization of (3-imidazol-1-ylpropyl)-(2-methyl-4-nitrophenyl)amine

A mixture of 130.1 g (0.5 mol) of (3-imidazol-1-ylpropyl)-(2-methyl-4-nitrophenyl)amine obtained above in the previous step and 28.25 g (0.25 mol) of 1,3-dichloropropane in 320 ml of normal pentanol was refluxed for 6 hours.

The reaction medium was a solution, which was cooled in an ice bath and absolute ethanol was added thereto: a gum precipitated out and then crystallized.

The crude product was filtered off, washed with absolute ethanol and dried at 40° C. under vacuum.

129.6 g of yellow crystals melting at 148–150° C. (Kofler) were obtained, the elemental analysis of which, calculated for $C_{29}H_{38}N_8O_4Cl_2.2.5H_2O$, was:

| % | C | H | N | O | Cl |
|---|---|---|---|---|---|
| calculated | 51.33 | 6.39 | 16.51 | 15.32 | 10.45 |
| found | 51.69 | 6.45 | 16.62 | 15.38 | 10.33 | c) Preparation of 1,3-bis{3-{3'-[(4"-amino-2"-methylanilino)-N-propyl]}-3H-imidazol-1-ium}propane dichloride tetrahydrochloride monohydrate diethanol The procedure described above in Example 1, step c) was used.

Starting with 100 g (0.1578 mol) of the product obtained above in the previous step, 111.0 g of white crystals melting with decomposition at 165–170° C. (Kofler) were obtained, the elemental analysis of which, calculated for $C_{29}H_{46}N_8Cl_6.H_2O.2CH_3CH_2OH$, was:

| % | C | H | N | O | Cl |
|---|---|---|---|---|---|
| calculated | 47.78 | 7.29 | 13.51 | 5.79 | 25.64 |
| found | 47.89 | 7.23 | 13.94 | 5.82 | 26.43 |

Preparation Example 3

Synthesis of 1,3-bis{3-{3'-[(4"-aminoanilino)-N-propyl]}-3H-imidazol-1-ium}propane dichloride tetrahydrochloride monohydrate ethanol

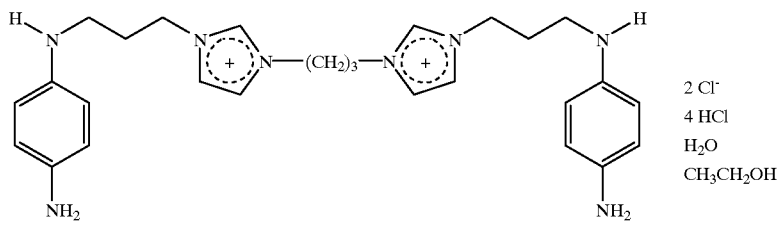

a) Preparation of (3-imidazol-1-ylpropyl)-(4-nitrophenyl)amine

A mixture of 150.2 g (1.2 mol) of 3-imidazol-1-ylpropylamine and 139.4 ml (1 mol) of triethylamine in 200 ml of dioxane was heated on a boiling water bath.

141.1 g (1 mol) of 1-fluoro-4-nitrobenzene were added dropwise over 30 minutes and the mixture was maintained at a temperature of 90–95° C. for 1 hour.

The crude product was poured into 2 kg of ice-cold water and the crystalline precipitate was filtered off, washed with water and recrystallized from refluxing 96° ethanol.

106.0 g of yellow crystals melting at 126° C. (Kofler) were obtained, the elemental analysis of which, calculated for $C_{12}H_{14}N_4O_2$, was:

| % | C | H | N | O |
|---|---|---|---|---|
| calculated | 58.53 | 5.73 | 22.75 | 12.99 |
| found | 58.33 | 5.83 | 22.81 | 13.41 | b) Preparation of 1,3-bis{3-{3'-[(4"-nitroanilino)-N-propyl]}-3H-imidazol-1-ium}propane dichloride 1/3 hydrate A mixture of 39.4 g (0.16 mol) of (3-imidazol-1-ylpropyl)-(4-nitrophenyl)amine obtained in the previous step and 9.03 g (0.08 mol) of 1,3-dichloropropane in 160 ml of toluene was refluxed for 6 hours. A gum in suspension crystallized out.

The suspension was cooled and the crystalline precipitate was filtered off, reimpasted twice in the minimum amount of absolute ethanol and dried at 45° C. under vacuum.

23.3 g of yellow crystals melting at 186° C. (Kofler) were obtained, the elemental analysis of which, calculated for $C_{27}H_{34}N_8O_4Cl_2 \cdot 1/3H_2O$, was:

| % | C | H | N | O | Cl |
|---|---|---|---|---|---|
| calculated | 53.03 | 5.71 | 18.32 | 11.34 | 11.59 |
| found | 53.00 | 5.68 | 18.33 | 11.19 | 11.44 | c) Reduction of 1,3-bis{3-{3'-[(4"-nitroanilino)-N-propyl]}-3H-imidazol-1-ium}propane dichloride 1/3 hydrate The procedure described above for Example 1, step c) was used.

Starting with 46.7 g (0.0771 mol) of 1,3-bis{3-{3'-[(4"-nitroanilino)-N-propyl]}-3H-imidazol-1-ium}propane dichloride 1/3 hydrate, 28.9 g of white crystals melting at about 148° C. and then at about 180° C. (Kofler) were obtained, the elemental analysis of which, calculated for $C_{27}H_{42}N_8Cl_6 \cdot H_2O \cdot CH_3CH_2OH$, was:

| % | C | H | N | O | Cl |
|---|---|---|---|---|---|
| calculated | 46.11 | 6.67 | 14.83 | 4.24 | 28.16 |
| found | 46.33 | 6.67 | 14.83 | 4.52 | 28.50 |

Preparation Example 4

Synthesis of 3,3-bis{3-{3'-[(4"-aminoanilino)-N-propyl]}-3H-imidazol-1-ium}-2-propanol dichloride tetrahydrochloride monohydrate a) Preparation of 1,3-bis{3-{3'-[(4"-nitroanilino)-N-propyl]}-3H-imidazol-1-ium}-2-propanol dichloride A mixture of 24.6 g (0.1 mol) of (3-imidazol-1-ylpropyl)-(4-nitrophenyl)amine obtained above in step a) of Example 3 and 6.45 g (0.05 mol) of 1,3-dichloro-2-propanol in 100 ml of toluene was refluxed for 8 hours. A gum in suspension crystallized out.

The suspension was cooled and the crystalline precipitate was filtered off, reimpasted twice in the minimum amount of absolute ethanol and dried at 45° C. under vacuum.

24.8 g of yellow crystals melting at 228–230° C. (Kofler) were obtained, the elemental analysis of which, calculated for $C_{27}H_{34}N_8O_5Cl_2$, was:

| % | C | H | N | O | Cl |
|---|---|---|---|---|---|
| calculated | 52.18 | 5.51 | 18.03 | 12.87 | 11.41 |
| found | 52.23 | 5.55 | 18.03 | 12.80 | 11.44 | b) Reduction of 1,3-bis{3-{3'-[(4"-nitroanilino)-N-propyl]}-3H-imidazol-1-ium}-2-propanol dichloride The procedure described above for Example 1, step c) was used.

Starting with 14.8 g (0.0238 mol) of 1,3-bis{3-{3'-[(4"-nitroaniiline)-N-propyl]}-3H-imidazol-1-ium}-2-propanol dichloride obtained above in the previous step, 8.9 g of cream-white crystals melting with decomposition at 160–170° C. (Kofler) were obtained, the elemental analysis of which, calculated for $C_{27}H_{42}N_8OCl_6 \cdot H_2O$, was:

| % | C | H | N | O | Cl |
|---|---|---|---|---|---|
| calculated | 44.71 | 6.11 | 15.45 | 4.41 | 29.32 |
| found | 44.90 | 6.18 | 15.43 | 4.71 | 29.61 |

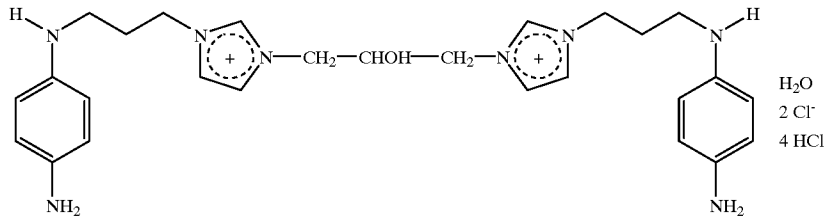

Preparation Example 5

Synthesis of N₁N₃-bis([3-N-(4'-aminoanilino)propyl]-1,1,3,3-tetramethyldiammonium)-1,3-propane dibromide tetrahydrobromide 1.5 hydrate

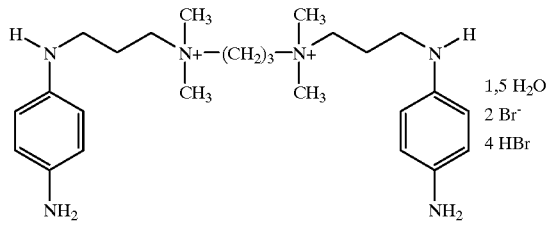

1,5 H₂O
2 Br⁻
4 HBr a) Preparation of N₁,N₃-bis{[3-N-(4'-nitroanilino)propyl]-1,1,3,3-tetramethyldiammonium}-1,3-propane dibromide monohydrate The procedure described for Example 3, step b) was used.

Starting with 44.6 g (0.2 mol) of N,N-dimethyl-N'-(4-nitrophenyl)propane-1,3-diamine and 20.2 g (0.1 mol) of 1,3-dibromopropane, 47.8 g of yellow crystals melting with decomposition at about 230° C. (Kofler) were obtained, the elemental analysis of which, Calculated for $C_{25}H_{40}N_6O_4Br_2 \cdot H_2O$ was

| % | C | H | N | O | Br |
|---|---|---|---|---|---|
| calculated | 45.06 | 6.35 | 12.61 | 12.00 | 23.98 |
| found | 45.15 | 6.35 | 12.36 | 11.61 | 24.02 | b) Reduction of N₁,N₃-bis{[3-N-(4'-nitroanilino)propyl]-1,1,3,3-tetramethyldiammonium}-1,3-propane dibromide 1.5 hydrate The procedure described for Example 1, step c) was used, the salification being carried out with aqueous hydrobromic acid.

Starting with 27.2 g (0.0408 mol) of N₁,N₃-bis{[3-N-(4'-nitroanilino)propyl]-1,1,3,3-tetramethyldiammonium}-1,3-propane dibromide tetrabromohydride monohydrate, 9.5 g of beige-coloured crystals melting with decomposition at 200–210° C. (Kofler) were obtained, the elemental analysis of which, calculated for $C_{25}H_{48}N_6Br_6 \cdot 1.5H_2O$, was:

| % | C | H | N | O | Br |
|---|---|---|---|---|---|
| calculated | 31.97 | 5.47 | 8.95 | 2.56 | 51.05 |
| found | 31.94 | 5.07 | 8.34 | 2.55 | 51.88 |

Prearatuion Example 6

Synthesis of 1,4-bis{3-[3-(2,5-diaminophenoxy)propyl]-3H-imidazol-1-ium}butane dichloride tetrahydrochloride dihydrate

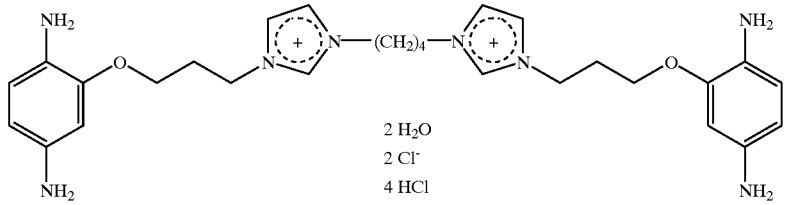

2 H₂O
2 Cl⁻
4 HCl a) Preparation of N-[2-(3-chloropropoxy)-4-nitrophenyl]acetamide A mixture of 98.1 g (0.5 mol) of N-(2-hydroxy-4-nitrophenyl)acetamide and 69.2 g (0.5 mol) of potassium carbonate in 500 ml of dimethylformamide was heated to 50° C. with stirring, 113.0 g (1 mol) of 1,3-dichloropropane were then added and heating at 50° C. was continued for 1 hour. The reaction mixture was poured into 4 litres of ice-cold water and the crystalline precipitate was filtered off, reimpasted in water and then in isopropyl alcohol and dried under vacuum at 40° C. over phosphorus pentoxide.

113.5 g of beige-coloured crystals which, after purification by recrystallization from refluxing isopropyl acetate, melted at 121° C. were obtained, the elemental analysis of which was in accordance with that calculated for $C_{11}H_{13}N_2O_4Cl$.

b) Quaternization of N-[2-(3-chloropropoxy)-4-nitrophenyl]acetamide 54.5 g (0.2 mol) of N-[2-(3-chloropropoxy)-4-nitrophenyl]acetamide obtained above in the previous step and 19.0 g (0.1 mol) of 1,4-diimidazol-1-ylbutane in 160 ml of 2-methyl-1-propanol were refluxed for 11 hours.

The mixture was cooled to room temperature and the oily precipitate was separated off after settling of the phase had taken place and taken up in absolute ethanol until crystallization.

After filtration, recrystallization from refluxing absolute ethanol and drying at 40° C. over potassium hydroxide, 65.9 g of pale yellow crystals melting at 132–134° C. (Kofler) were obtained, the ¹H NMR of which was in accordance.

c) Preparation of 1,4-bis{3-[3-(2,5-diaminophenoxy)propyl]-3H-imidazol-1-ium}butane dichloride tetrahydrochloride dihydrate The procedure described for Example 1, step c) was used, without salifying the reduced compound.

Starting with 77.7 g (0.105 mol) of the compound obtained above in the previous step, 59.0 g of a brown oil were obtained.

This oily compound was dissolved in 110 ml of aqueous 36% hydrochloric acid and heated for 45 minutes on a boiling water bath.

The mixture was cooled to room temperature (solution), diluted with 100 ml of ethanol and recooled in an ice bath.

The crystalline precipitate was filtered off, washed with absolute ethanol and dried under vacuum over potassium hydroxide.

34.0 g of white crystals melting with decomposiiton at 230° C. (Kofler) were obtained, the elemental analysis of which, calculated for $C_{28}H_{44}N_8O_2Cl_6 \cdot 2H_2O$, was:

| % | C | H | N | O | Cl |
|---|---|---|---|---|---|
| calculated | 43.48 | 6.26 | 14.49 | 8.27 | 27.50 |
| found | 43.71 | 6.18 | 14.48 | 8.06 | 27.80 |

Preparation Example 7

Synthesis of 1,3-bis[3-(2,5-diaminophenoxy)propyl]-3H-imidazol-1-ium monochloride tetrahydrochloride monohydrate

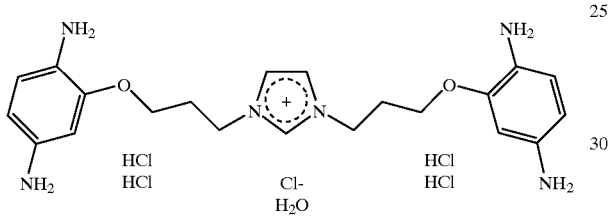

a) Preparation of N-[2-(3-imidazol-1-ylpropoxy)-4-nitrophenyl]acetamide 54.5 g (0.2 mol) of N-[2-(3-chloropropoxy)-4-nitrophenyl]acetamide, the preparation of which was described in step a) of Example 6 above, and 40.8 g (0.6 mol) of 1H imidazole in 150 ml of dimethylformamide were heated on a boiling water bath for 4 hours.

The mixture was poured onto 900 g of ice-cold water and the crystalline precipitate was filtered off, washed with water and recrystallized from refluxing isopropanol.

After drying at 45° C. under vacuum, 30.2 g of pale yellow crystals melting at 139° C. (Kofler) were obtained, the elemental analysis of which was in accordance with that calculated for $C_{14}H_{16}N_4O_4$.

b) Preparation of 1,3-bis[3-(2-acetylamino-5-nitrophenoxy)propyl]-3H-imidazol-1-ium chloride The procedure described above for Example 6, step b) was used.

Starting with 18.9 g (0.062 mol) of N-[2-(3-imidazol-1-ylpropoxy)-4-nitrophenyl]acetamide obtained in the previous step and 18.6 g (0.068 mol) of N-[2-(3-chloropropoxy)-4-nitrophenyl]acetamide, the preparation of which was described in step a) of Example 6 above, and after recrystallization from a refluxing water/ethanol mixture, 28.2 g of pale yellow crystals of 1,3-bis[3-(2-acetylamino-5-nitrophenoxy)propyl]-3H-imidazol-1-ium chloride melting at 190° C. (Kofler) were obtained, the elemental analysis of which was in accordance with that calculated for $C_{25}H_{29}N_6O_8Cl$.

c) Reduction of 1,3-bis[3-(2-acetylamino-5-nitrophenoxy)propyl]-3H-imidazol-1-ium chloride The procedure described for Example 1, step c), was used, without salifying the reduced compound.

Starting with 28.0 g (0.0485 mol) of 1,3-bis[3-(2-acetylamino-5-nitrophenoxy)propyl]-3H-imidazol-1-ium chloride synthesized above in the previous step, 23.5 g of white crystals of 1,3-bis[3-(2-acetylamino-5-aminophenoxy)propyl]-3H-imidazol-1-ium chloride were obtained, the elemental analysis of which was in accordance with that calculated for $C_{25}H_{33}N_6O_4Cl$.

d) Deacetylation of 1,3-bis[3-(2-acetylamino-5-aminophenoxy)propyl]-3H-imidazol-1-ium chloride The procedure described for Example 6, step c) is used.

Starting with 23.5 g (0.0454 mol) of 1,3-bis [3-(2-acetylamino-5-aminophenoxy)propyl]-3H-imidazol-1-ium chloride synthesized above in the previous step, 15.0 g of white crystals melting with decomposition at 210–215° C. (Kofler) were obtained, the $^1$H NMR of which was in accordance and the elemental analysis of which, calculated for $C_{21}H_{33}N_6O_2Cl_5 \cdot H_2O$, was:

| % | C | H | N | O | Cl |
|---|---|---|---|---|---|
| calculated | 42.26 | 5.91 | 14.08 | 8.04 | 29.70 |
| found | 41.89 | 6.03 | 13.98 | 9.32 | 30.11 |

Preparation Example 8

Synthesis of $N_1,N_4$-bis{[3-N-methyl-N-(4'-aminoanilino)ethyl]-1,1,4,4-tetramethyldiammonium}-1,3-propane dibromide dihydrobromide monohydrate

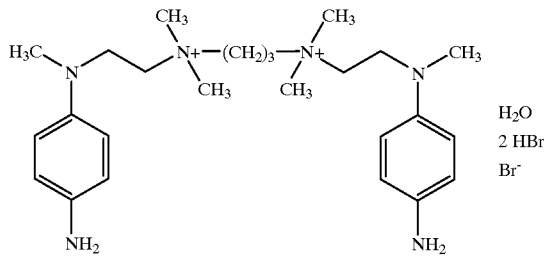

a) Preparation of $N_1,N_4$-bis{[3-N-methyl-N-(4'-nitroanilino)ethyl]-1,1,4,4-tetramethyldiammonium}-1,3-propane dibromide monohydrate The procedure described for Example 4, step a) is used, but using 2-methyl-1-propanol as solvent instead of toluene.

Starting with 53.6 g (0.24 mol) of N,N,N'-trimethyl-N'-(4-nitrophenyl)ethane-1,2-diamine and 24.2 g (0.12 mol) of 1,3-dibromopropane, 63.5 g of yellow crystals melting at about 147° C. (Kofler) were obtained, the elemental analysis of which, calculated for $C_{25}H_{40}N_6O_4Br_2 \cdot H_2O$, was:

| % | C | H | N | O | Br |
|---|---|---|---|---|---|
| calculated | 45.06 | 6.35 | 12.61 | 12.00 | 23.98 |
| found | 45.04 | 6.38 | 12.60 | 12.68 | 23.98 | b) Reduction of $N_1,N_4$-bis{[3-N-methyl-N-(4'-nitroanilino)ethyl]-1,1,4,4-tetramethyldiammonium}-1,3-prolane dibromide monohydrate The procedure described for Example 1, step c) is used, the salification being carried out with aqueous hydrobromic acid.

Starting with 48.5 g (0.075 mol) of $N_1,N_4$-bis{[3-N-methyl-N-(4'-nitroanilino)ethyl]-1,1,4,4- tetramethyldiammonium}-1,3-propane dibromide monohydrate, and after recrystallization from a refluxing water/ethanol mixture, 27.8 g of cream-coloured crystals melting at a temperature above 260° C. (Kofler) were obtained, the elemental analysis of which, calculated for $C_{25}H_{46}N_6Br_4 \cdot H_2O$, was:

| % | C | H | N | O | Br |
|---|---|---|---|---|---|
| calculated | 39.08 | 6.30 | 10.94 | 2.08 | 41.60 |
| found | 39.23 | 6.28 | 10.85 | 1.49 | 42.38 |

Preparation Example 9

Synthesis of 1,4-bis[3-(5-amino-2-hydroxybenzyl)-3H-imidazol-1-ium]butane dihydrochloride monohydrate

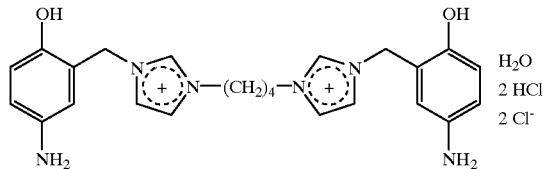

a) Preparation of 1,4-bis[3-(5-nitro-2-hydroxybenzyl)-3H-imidazol-1-ium]butane dichloride monohydrate 37.5 g (0.2 mol) of 2-chloromethyl-4-nitrophenol and 19.0 g (0.1 mol) of 1,4-diimidazol-1-ylbutane in 200 ml of toluene were heated for 8 hours on a boiling water bath.

The gum in suspension was separated out after settling had taken place and was taken up in absolute ethanol until crystallization was complete.

After filtration and recrystallization from a refluxing ethanol/water mixture, 31.3 g of yellow crystals melting at a temperature above 260° C. (Kofler) were obtained, the elemental analysis of which, calculated for $C_{24}H_{26}N_6O_6Cl_2 \cdot H_2O$, was:

| % | C | H | N | O | Cl |
|---|---|---|---|---|---|
| calculated | 49.41 | 4.84 | 14.40 | 19.20 | 12.15 |
| found | 49.55 | 4.80 | 14.18 | 19.76 | 12.10 | b) Reduction of 1,4-bis[3-(5-nitro-2-hydroxybenzyl)-3H-imidazol-1-ium]butane dichloride monohydrate The procedure described for Example 1, step c) was used.

Starting with 31.0 g (0.055 mol) of 1,4-bis[3-(5-nitro-2-hydroxybenzyl)-3H-imidazol-1-ium]butane dichloride monohydrate synthesized above in the previous step, 24.8 g of white crystals melting at a temperature above 260° C. (Kofler) were obtained, the structure of which was in accordance by $^1$H NMR.

Preparation Example 10

Synthesis of 1,3-bis{3-[3-(2,5-diaminophenoxy)propyl]-3H-imidazol-1-ium}propane dichloride tetrahydrochloride dehydrate

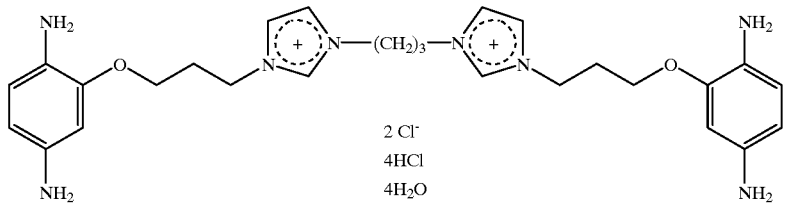

a) Preparation of 1,3-bis{3-[3-(2-acetylamino-5-nitrophenoxy)propyl]-3H-imidazol-1-ium}propane dichloride+1.5 $H_2O$ A mixture of 27.4 g (0.09 mol) of N-[2-(3-imidazol-1-ylpropoxy)-4-nitrophenyl]acetamide, the preparation of which was described above in Example 7, step a), and 5.1 g (0.045 mol) of 1,3-dichloropropane in 60 ml of 1-pentanol was refluxed for 10 hours.

The mixture was cooled to room temperature and the crystalline precipitate was filtered off, washed with absolute ethanol and recrystallized from refluxing 96° ethanol.

23.7 g of pale yellow crystals of 1,3-bis{3-[3-(2-acetylamino-5-nitrophenoxy)propyl]-3H-imidazol-1-ium}propane dichloride+1.5$H_2O$ melting at 187–188° C. were obtained, the elemental analysis of which, calculated for $C_{31}H_{38}N_8O_8Cl_2 \cdot 1.5H_2O$, was:

| % | C | H | N | O | Cl |
|---|---|---|---|---|---|
| calculated | 49.74 | 5.52 | 14.97 | 20.30 | 9.47 |
| found | 49.76 | 5.61 | 14.93 | 20.30 | 9.71 | b) Reduction and deacetylation of 1,3-bis{3-[3-(2-acetylamino-5-nitrophenoxy)propyl]-3H-imidazol-1-ium}propane dichloride+1.5$H_2O$ 25.3 g (0.0338 mol) of 1,3-bis{3-[3-(2-acetylamino-5-nitrophenoxy)propyl]-3H-imidazol-1-ium}propane dichloride+1.5$H_2O$ obtained above in the previous step, 16 g of 5% palladium on charcoal (containing 50% water), 300 ml of ethanol and 300 ml of water were placed in a hydrogenator. The reduction took place over one hour under a hydrogen pressure of about 8 bar and at a temperature which was gradually raised to 80° C. 22.2 g of a lacquer of 1,3-bis{3-[3-(2-acetylamino-5-aminophenoxy)propyl]-3H-imidazol-1-ium}propane dichloride were obtained, which product was heated for ½ hour on a boiling water bath in 42 ml of aqueous 36% hydrochloric acid.

The mixture was cooled in an ice bath and diluted with 100 ml of absolute ethanol. The crystalline precipitate was filtered off, washed with absolute ethanol and dried under vacuum at 50° C. over phosphorus pentoxide.

19.0 g of white crystals of 1,3-bis{3-[3-(2,5-diaminophenoxy)propyl]-3H-imidazol-1-ium}propane dichloride tetrahydrochloride dihydrate melting with decomposition at 218–220° C. were obtained, the elemental analysis of which, calculated for $C_{27}H_{42}N_8O_2Cl_6 \cdot 2H_2O$, was:

| % | C | H | N | O | Cl |
|---|---|---|---|---|---|
| calculated | 42.70 | 6.11 | 14.75 | 8.43 | 28.01 |
| found | 43.19 | 6.12 | 14.76 | 8.42 | 28.56 |

APPLICATION EXAMPLES

Examples 1 to 11 of Dyeing in Basic Medium

The following dye compositions were prepared (contents in grams):

| EXAMPLE | 1 | 2 | 3 | 4 | 5 | 6 | 7 | 8 | 9 | 10 | 11 |
|---|---|---|---|---|---|---|---|---|---|---|---|
| 1,4-Bis{3-[3-(2,5-diaminophenoxy)propyl]-3H-imidazol-1-ium}butane dichloride tetrahydrochloride dihydrate (compound of formula (I)) | 1.159 | 1.159 | — | — | — | — | — | — | — | — | — |
| 1,3-Bis[3-(2,5-diaminophenoxy)propyl]-3H-imidazol-1-ium monochloride tetrahydrochloride monohydrate (compound of formula (I)) | — | — | 0.894 | — | — | — | — | — | — | — | — |
| $N_1,N_4$-Bis{[3-N-methyl-N-(4'-aminoanilino)ethyl]-1,1,4,4-tetramethyldiammonium}-1,3-propane dibromide dihydrobromide monohydrate (compound of formula (I)) | — | — | — | 1.152 | 1.152 | — | — | — | — | — | — |
| 1,3-Bis{3-{3'[(4"-amino-3"-methylanilino)-N-propyl]}-3H-imidazol-1-ium}propane dichloride tetrahydrochloride 1/3 ethanol monohydrate (compound of formula (I)) | — | — | — | — | — | 1.083 | 1.083 | — | — | — | — |
| 1,3-Bis{3-{3'-[(4"-amino-2"-methylanilino)-N-propyl]}-3H-imidazol-1-ium}propane dichloride tetrahydrochloride monohydrate diethanol (compound of formula (I)) | — | — | — | — | — | — | — | 1.243 | 1.243 | — | — |
| 1,3-Bis{3-{3'-[(4"-aminoanilino)-N-propyl]}-3H-imidazol-1-ium}propane dichloride tetrahydrochloride monohydrate ethanol (compound of formula (I)) | — | — | — | — | — | — | — | — | — | 1.132 | 1.132 |
| Resorcinol (coupler) | — | — | 0.33 | — | — | — | — | — | — | — | — |
| meta-Aminophenol (coupler) | — | — | — | — | — | 0.327 | — | — | — | — | — |
| 2-Methyl-5-N-(β-hydroxyethyl) aminophenol (coupler) | — | 0.543 | — | 0.543 | — | — | — | — | 0.543 | — | — |
| 2,4-Diaminophenoxyethanol dihydrochloride (coupler) | — | — | — | — | — | — | 0.675 | — | — | — | 0.675 |
| Common dye support | (*) | (*) | (*) | (*) | (*) | (*) | (*) | (*) | (*) | (*) | (*) |
| Demineralized water q.s. | 100 g | 100 g | 100 g | 100 g | 100 g | 100 g | 100 g | 100 g | 100 g | 100 g | 100 g |

(*) Common dye support:
    96° Ethanol      20 g
    Pentasodium salt of diethylenetriamine-pentaacetic acid sold under the name Masquol DTPA by the company Protex      1.08 g
    Sodium metabisulphite as an aqueous 20%      0.58 g A.M.
    Aqueous ammonia      10 g At the time of use, each of the above dye compositions was mixed, weight for weight, with a 20-volumes hydrogen peroxide solution (6% by weight) of pH 3.

The mixture obtained was applied to locks of natural or permanent-waved grey hair containing 90% white hairs, for 30 minutes. The locks were then rinsed, washed with a standard shampoo, rinsed again and then dried.

The shades obtained are given in the table below:

| EXAMPLE | DYEING pH | Shade on natural hair | Shade on permanent-waved hair |
|---|---|---|---|
| 1 | 10 ± 0.2 | Golden-ash natural dark blonde | Ash-light blonde |
| 2 | 10 ± 0.2 | Blue | Purple-chestnut |
| 3 | 10 ± 0.2 | Slightly matt ash-chestnut | Golden-ash natural light chestnut |
| 4 | 10 ± 0.2 | Blue | Iridescent purple light blonde |
| 5 | 10 ± 0.2 | Matt light-chestnut | Violet-ash chestnut |
| 6 | 10 ± 0.2 | Matt grey | Dark grey |
| 7 | | Dull green-blue | Green-blue |
| 8 | 10 ± 0.2 | Iridescent mahogany | Mahogany |
| 9 | 10 ± 0.2 | Iridescent purple | Iridescent purple |
| 10 | 10 ± 0.2 | Ash-golden dark blonde | Ash light chestnut |
| 11 | 10 ± 0.2 | Blue | Blue |

What is claimed is:

1. A compound of formula (I), or an acid addition salt thereof:

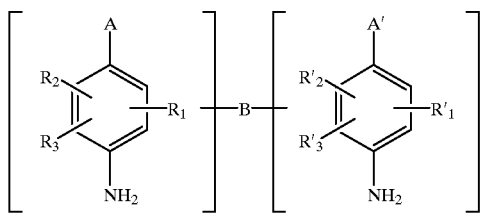

(I)

wherein:

B is a divalent linker arm which represents a group Z or an alkyl chain, said alkyl chain being uninterrupted or interrupted by at least one group Z and/or by at least one hetero atom, said alkyl chain being unsubstituted or substituted with at least one radical selected from hydroxyl and $C_1$–$C_6$ alkoxy radicals, said alkyl chain having no ketone functions or at least one ketone function;

$R_1$, $R_2$, $R_3$, $R'_1$, $R'_2$ and $R'_3$, are identical or different and represent a divalent linker arm B, a hydrogen atom;

a halogen atom;

a group Z;

a ($C_1$–$C_6$)alkylcarbonyl radical;

an amino($C_1$–$C_6$)alkylcarbonyl radical;

an N-Z-amino($C_1$–$C_6$)alkylcarbonyl radical;

an N-($C_1$–$C_6$)alkylamino($C_1$–$C_6$)alkylcarbonyl radical;

an N,N-di($C_1$–$C_6$)alkylamino($C_1$–$C_6$)alkylcarbonyl radical;

an amino($C_1$–$C_6$)alkylcarbonyl($C_1$–$C_6$)alkyl radical;

an N-Z-amino($C_1$–$C_6$)alkylcarbonyl($C_1$–$C_6$)alkyl radical;

an N-($C_1$–$C_6$)alkylamino($C_1$–$C_6$)alkylcarbonyl($C_1$–$C_6$) alkyl radical;

an N,N-di($C_1$–$C_6$)alkylamino($C_1$–$C_6$)alkylcarbonyl ($C_1$–$C_6$)alkyl radical;

a carboxyl radical;

a ($C_1$–$C_6$)alkylcarboxyl radical;

a $C_1$–$C_6$ alkylsulphonyl radical;

an aminosulphonyl radical;

an N-Z-aminosulphonyl radical;

a $C_1$–$C_6$ N-alkylaminosulphonyl radical;

an N,N-di($C_1$–$C_6$)alkylaminosulphonyl radical;

an aminosulphonyl($C_1$–$C_6$)alkyl radical;

an N-Z-aminosulphonyl($C_1$–$C_6$)alkyl radical;

an N-($C_1$–$C_6$)alkylaminosulphonyl($C_1$–$C_6$)alkyl radical;

an N,N-di($C_1$–$C_6$)alkylaminosulphonyl($C_1$–$C_6$)alkyl radical;

a carbamyl radical;

an N-($C_1$–$C_6$)alkylcarbamyl radical;

an N,N-di($C_1$–$C_6$)alkylcarbamyl radical;

a carbamyl($C_1$–$C_6$)alkyl radical;

an N-($C_1$–$C_6$)alkylcarbamyl($C_1$–$C_6$)alkyl radical;

an N,N-di($C_1$–$C_6$)alkylcarbamyl($C_1$–$C_6$)alkyl radical;

a $C_1$–$C_6$ alkyl radical;

a monohydroxy($C_1$–$C_6$)alkyl radical;

a polyhydroxy($C_2$–$C_6$)alkyl radical;

a ($C_1$–$C_6$)alkoxy($C_1$–$C_6$)alkyl radical;

a trifluoro($C_1$–$C_6$)alkyl radical;

a cyano radical;

a group $OR_6$ a group $SR_6$;

an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$)alkylcarbonyl, N-Z-amino($C_1$–$C_6$) alkylcarbonyl, N-($C_1$–$C_6$)alkylamino($C_1$–$C_6$) alkylcarbonyl, N,N-di($C_1$–$C_6$)alkylamino($C_1$–$C_6$) alkylcarbonyl, carbamyl, N-($C_1$–$C_6$)alkylcarbamyl, N,N-di($C_1$–$C_6$)alkylcarbamyl, $C_1$–$C_6$ alkylsulphonyl, aminosulphonyl, N-Z-aminosulphonyl, $C_1$–$C_6$ N-alkylaminosulphonyl, N,N-di($C_1$–$C_6$) alkylaminosulphonyl, thiocarbamyl or formyl radical, or with a group Z;

$R_6$ represents a divalent linker arm B, a $C_1$–$C_6$ alkyl radical;

a monohydroxy($C_1$–$C_6$)alkyl radical;

a polyhydroxy($C_2$–$C_6$)alkyl radical;

a group Z;

a ($C_1$–$C_6$)alkoxy($C_1$–$C_6$)alkyl radical;

an aryl radical;

a benzyl radical;

a carboxy($C_1$–$C_6$)alkyl radical;

a ($C_1$–$C_6$)alkylcarboxy($C_1$–$C_6$)alkyl radical;

a cyano($C_1$–$C_6$)alkyl radical;

a carbamyl($C_1$–$C_6$)alkyl radical;

an N-($C_1$–$C_6$)alkylcarbamyl($C_1$–$C_6$)alkyl radical;

an N,N-di($C_1$–$C_6$)alkylcarbamyl($C_1$–$C_6$)alkyl radical;

a trifluoro($C_1$–$C_6$)alkyl radical;

an aminosulphonyl($C_1$–$C_6$)alkyl radical;

an N-Z-aminosulphonyl($C_1$–$C_6$)alkyl radical;

an N-($C_1$–$C_6$)alkylaminosulphonyl($C_1$–$C_6$)alkyl radical;

an N,N-di($C_1$–$C_6$)alkylaminosulphonyl($C_1$–$C_6$)alkyl radical;

a ($C_1$–$C_6$)alkylsulphinyl($C_1$–$C_6$)alkyl radical;

a ($C_1$–$C_6$)alkylsulphonyl($C_1$–$C_6$)alkyl radical;

a ($C_1$–$C_6$)alkylcarbonyl($C_1$–$C_6$)alkyl radical;

an amino($C_1$–$C_6$)alkyl radical;

an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$)alkylcarbonyl, ($C_1$–$C_6$)alkylcarboxyl, carbamyl, N-($C_1$–$C_6$)alkylcarbamyl, N,N-di($C_1$–$C_6$)alkylcarbamyl, thiocarbamyl and $C_1$–$C_6$ alkylsulphonyl radicals, or with a group Z;

A represents a group —$NR_4R_5$ or a hydroxyl radical;

A' represents a group —$NR'_4R'_5$ or a hydroxyl radical;

$R_4$, $R_5$, $R'_4$ and $R'_5$, are identical or different and represent a divalent linker arm B, a hydrogen atom;

a group Z;

a $C_1$–$C_6$ alkyl radical;

a monohydroxy($C_1$–$C_6$)alkyl radical;

a polyhydroxy($C_2$–$C_6$)alkyl radical;

a ($C_1$–$C_6$)alkoxy($C_1$–$C_6$)alkyl radical;

an aryl radical;

a benzyl radical;

a cyano($C_1$–$C_6$)alkyl radical;

a carbamyl($C_1$–$C_6$)alkyl radical;

an N-($C_1$–$C_6$)alkylcarbamyl($C_1$–$C_6$)alkyl radical;

an N,N-di($C_1$–$C_6$)alkylcarbamyl($C_1$–$C_6$)alkyl radical;

a thiocarbamyl($C_1$–$C_6$)alkyl radical;

a trifluoro($C_1$–$C_6$)alkyl radical;

a sulpho($C_1$–$C_6$)alkyl radical;

a ($C_1$–$C_6$)alkylcarboxy($C_1$–$C_6$)alkyl radical;

a ($C_1$–$C_6$)alkylsulphinyl($C_1$–$C_6$)alkyl radical;

an aminosulphonyl($C_1$–$C_6$)alkyl radical;

an N-Z-aminosulphonyl($C_1$–$C_6$)alkyl radical;

an N-($C_1$–$C_6$)alkylaminosulphonyl($C_1$–$C_6$)alkyl radical;

an N,N-di($C_1$–$C_6$)alkylaminosulphonyl($C_1$–$C_6$)alkyl radical;

a ($C_1$–$C_6$)alkylcarbonyl($C_1$–$C_6$)alkyl radical;

an amino($C_1$–$C_6$)alkyl radical;

an amino($C_1$–$C_6$)alkyl radical wherein the amine is substituted with one or two identical or different radicals selected from alkyl, monohydroxy($C_1$–$C_6$)alkyl, polyhydroxy($C_2$–$C_6$)alkyl, ($C_1$–$C_6$)alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z is selected from the unsaturated cationic groups of formulae (II) and (III) below, and the saturated cationic groups of formula (IV) below:

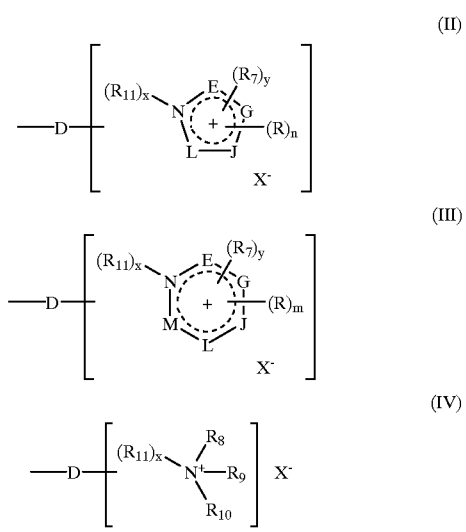

wherein:

D is a divalent linker arm which represents a linear or branched alkyl chain, said alkyl chain being uninterrupted or interrupted by at least one hetero atom, and said alkyl chain being unsubstituted or substituted with at least one hydroxyl or $C_1$–$C_6$ alkoxy radical, said alkyl chain having no ketone function or at least one ketone function;

the ring members E, G, J, L and M, are identical or different and represent a carbon, oxygen, sulphur or nitrogen atom;

n is an integer ranging from 0 to 4 inclusive;

m is an integer ranging from 0 to 5 inclusive;

the radicals R, are identical or different and represent a divalent linker arm B, a group Z, a halogen atom, a hydroxyl radical, a $C_1$–$C_6$ alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a thio($C_1$–$C_6$)alkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical;

a group NHR" or NR"R'" wherein R" and R'" are identical or different and represent a $C_1$–$C_6$ alkyl radical, a monohydroxy($C_1$–$C_6$)alkyl radical or a polyhydroxy($C_2$–$C_6$)alkyl radical;

$R_7$ represents a divalent linker arm B, a $C_1$–$C_6$ alkyl radical, a monohydroxy($C_1$–$C_6$)alkyl radical, a polyhydroxy($C_2$–$C_6$)alkyl radical, a cyano($C_1$–$C_6$)alkyl radical, a tri($C_1$–$C_6$)alkylsilane($C_1$–$C_6$)alkyl radical, a ($C_1$–$C_6$)alkoxy($C_1$–$C_6$)alkyl radical, a carbamyl($C_1$–$C_6$)alkyl radical, a ($C_1$–$C_6$)alkylcarboxy($C_1$–$C_6$)alkyl radical, a benzyl radical a group Z of formula (II), (III) or (IV) as defined above;

$R_8$, $R_9$ and $R_{10}$, are identical or different and represent a divalent linker arm B, a $C_1$–$C_6$ alkyl radical, a monohydroxy($C_1$–$C_6$)alkyl radical, a polyhydroxy($C_2$–$C_6$)alkyl radical, a ($C_1$–$C_6$)alkoxy($C_1$–$C_6$)alkyl radical, a cyano($C_1$–$C_6$)alkyl radical, an aryl radical, a benzyl radical, an amido($C_1$–$C_6$)alkyl radical, a tri($C_1$–$C_6$)alkylsilane($C_1$–$C_6$)alkyl radical an amino($C_1$–$C_6$)alkyl radical wherein the amine is protected with a ($C_1$–$C_6$)alkylcarbonyl, carbamyl or $C_1$–$C_6$ alkylsulphonyl radical; two of the radicals $R_8$, $R_9$ and $R_{10}$ may together form, with the nitrogen atom to which they are attached, a saturated 5- or 6-membered ring, wherein said ring may contain at least one additional hetero atom, wherein said ring is unsubstituted or substituted with a halogen atom, a hydroxyl radical, a $C_1$–$C_6$ alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a thio($C_1$–$C_6$)alkyl radical, a $C_1$–$C_6$ alkylthio radical, an amino radical an amino radical protected with a ($C_1$–$C_6$) alkylcarbonyl, carbamyl or $C_1$–$C_6$ alkylsulphonyl radical;

one of the radicals $R_8$, $R_9$ and $R_{10}$ may represent a second group Z which is identical to or different from the first group Z;

$R_{11}$ represents a divalent linker arm B, a $C_1$–$C_6$ alkyl radical;

a monohydroxy($C_1$–$C_6$)alkyl radical;

a polyhydroxy($C_2$–$C_6$)alkyl radical;

an aryl radical;

a benzyl radical;

an amino($C_1$–$C_6$)alkyl radical, an amino($C_1$–$C_6$)alkyl radical wherein the amine is protected with a ($C_1$–$C_6$)alkylcarbonyl, carbamyl or $C_1$–$C_6$ alkylsulphonyl radical;

a carboxy($C_1$–$C_6$)alkyl radical;

a cyano($C_1$–$C_6$)alkyl radical;

a carbamyl($C_1$–$C_6$)alkyl radical;

a trifluoro($C_1$–$C_6$)alkyl radical;

a tri($C_1$–$C_6$)alkylsilane($C_1$–$C_6$)alkyl radical;

a sulphonamido($C_1$–$C_6$)alkyl radical;

a ($C_1$–$C_6$)alkylcarboxy($C_1$–$C_6$)alkyl radical;

a ($C_1$–$C_6$)alkylsulphinyl($C_1$–$C_6$)alkyl radical;

a ($C_1$–$C_6$)alkylsulphonyl($C_1$–$C_6$)alkyl radical;

a ($C_1$–$C_6$)alkylketo($C_1$–$C_6$)alkyl radical;

an N-($C_1$–$C_6$)alkylcarbamyl($C_1$–$C_6$)alkyl radical;

an N-($C_1$–$C_6$)alkylsulphonamido($C_1$–$C_6$)alkyl radical;

x and y are integers equal to 0 or 1; with the proviso that:
 in the unsaturated cationic group of formula (II):
  when x=0, the divalent linker arm D is attached to the nitrogen atom,
  when x=1, the divalent linker arm D is attached to one of the ring members E, G, J or L,
  y can take the value 1 only:
   1) when the ring members E, G, J and L simultaneously represent a carbon atom and when the radical $R_7$ is connected to the nitrogen atom of the unsaturated ring; or
   2) when at least one of the ring members E, G, J and L represents a nitrogen atom to which the radical $R_7$ is attached;
 in the unsaturated cationic group of formula (III):
  when x=0, the divalent linker arm D is attached to the nitrogen atom,
  when x=1, the divalent linker arm D is attached to one of the ring members E, G, J, L or M,
  y can take the value 1 only when at least one of the ring members E, G, J, L and M represents a divalent atom and when the radical $R_7$ is connected to the nitrogen atom of the unsaturated ring;
 in the cationic group of formula (IV):
  when x=0, then the divalent linker arm is attached to the nitrogen atom bearing the radicals $R_8$ to $R_{10}$,
  when x=1, then two of the radicals $R_8$ to $R_{10}$ form, together with the nitrogen atom to which they are attached, a saturated 5- or 6-membered ring as defined above, and the divalent linker arm D is connected to a carbon atom of said saturated ring;

$X^-$ represents a monovalent or divalent anion; and further with the proviso that:
 the number of cationic groups Z in said compound or acid addition salt thereof is at least equal to 1.

2. A compound of formula (I) or salt thereof according to claim 1, wherein said divalent linker arm B represents an alkyl chain having from 1 to 14 linear carbon atoms or 3 to 14 branched carbon atoms.

3. A compound of formula (I) or salt thereof according to claim 2, wherein said alkyl chain is interrupted by at least one hetero atom selected from oxygen, sulfur, and nitrogen atoms.

4. A compound of formula (II) or (III) or (IV) or salt thereof according to claim 1, wherein said divalent linker arm D represents an alkyl chain having from 1 to 14 linear carbon atoms or 3 to 14 branched carbon atoms.

5. A compound of formula (II) or (III) or (IV) or salt thereof according to claim 4, wherein said alkyl chain is interrupted by at least one hetero atom selected from oxygen, sulfur, and nitrogen atoms.

6. A compound or salt thereof according to claim 1, wherein said unsaturated cationic Z group of formula (II) is selected from quaternized pyrrole, imidazole, pyrazole, oxazole, thiazole and triazole rings.

7. A compound or salt thereof according to claim 1, wherein said unsaturated cationic Z group of formula (III) is selected from quaternized pyridine, pyrimidine, pyrazine, oxazine and triazine rings.

8. A compound or salt thereof according to claim 1, wherein two of said radicals $R_8$, $R_9$ and $R_{10}$, together with the nitrogen atom to which they are attached, form a quaternized pyrrolidine, piperidine, piperazine or a morpholine ring.

9. A compound according to claim 1 wherein said $X^-$ is an anion selected from a halogen atom, a hydroxide, a hydrogenosulphate and a $C_1$–$C_6$ alkyl sulphate.

10. A compound according to claim 1, wherein said compound is:

1,3-bis{3-{3'-[(4"-amino-3"-methylanilino)-N-propyl]}-3H-imidazol-1-ium}propane dichloride;

1,3-bis{3-{3'-[(4"-amino-2"-methylanilino)-N-propyl]}-3H-imidazol-1-ium}propane dichloride monohydrate diethanol;

1,3-bis{3-{3'-[(4"-aminoanilino)-N-propyl]}-3H-imidazol-1-ium}propane dichloride monohydrate ethanol;

1,3-bis{3-{3'-[(4"-aminoanilino)-N-propyl]}-3H-imidazol-1-ium}-2-propanol dichloride monohydrate;

$N_1,N_3$-bis[3-N-(4'-aminoanilino)propyl]-1,1,3,3-tetramethyldiammonium 1-3 propane dibromide monohydrate;

1,4-bis{3-[3-(2,5-diaminophenoxy)propyl]-3H-imidazol-1-ium}butane dichloride dihydrate;

1,3-bis[3-(2,5-diaminophenoxy)propyl]-3H-imidazol-1-ium monochloride monohydrate;

$N_1,N_4$-bis[3-N-methyl-N-(4'-aminoanilino)ethyl]-1,1,4,4-tetramethyldiammonium 1-3-propane dibromide monohydrate;

1,4-bis[3-(5-amino-2-hydroxybenzyl)-3H-imidazol-1-ium]butane dichloride monohydrate;

1,3-bis{[2-(4-aminoanilino)propyl]-1,1,3,3-tetramethyldiammoniumpropane dibromide;

1,3-bis{[4-(4-aminoanilino)pentyl]-1,1,3,3-tetramethyldiammonium}propane dichloride;

[4-(4-aminophenylamino)pentyl]-(5-amino-2-hydroxybenzyl)diethylammonium monochloride;

[2-(4-aminophenylamino)propyl]-(5-amino-2-hydroxybenzyl)dimethylammonium monochloride;

1,3-bis{3-[3-(2,5-diaminophenoxy)propyl]-3H-imidazol-1-ium}propane dichloride dihydrate;

1,3-bis{3-{3'-[(4"-aminoanilino)-N-propyl]}-3H-imidazol-1-ium}propane dichloride;

1,3-bis{4-{4'-(4-[3-(4"-aminophenylamino)propyl]}-1,3-dimethyl-3H-imidazol-1-ium}propane dichloride, 1,3-bis{4-{4'-(4-[3-(4"-amino-2"-methylanilino)-propyl}-1,3-dimethyl-3H-imidazol-1-ium}propane dichloride;

4-[2-(2,5-diaminophenoxy)ethyl]-3-[3-(2,5-diaminophenoxy)propyl]-1-methyl-3-imidazol-1-ium monochloride;

4-[2-(2,5-diaminophenoxy)ethyl]-1-[3-(2,5-diaminophenoxy)propyl]-3-methyl-3-imidazol-1-ium monochloride; or an acid addition salt thereof.

11. A compound according to claim 10, wherein said compound is:

1,3-bis{3-{3'-[(4"-aminoanilino)-N-propyl]}-3H-imidazol-1-ium}propane dichloride monohydrate ethanol;

1,3-bis[3-(2,5-diaminophenoxy)propyl]-3H-imidazol-1-ium monochloride monohydrate;

$N_1,N_4$-bis[3-N-methyl-N-(4'-aminoanilino)ethyl]-1,1,4,4-tetramethyidiammonium 1-3-propane dibromide monohydrate;

1,4-bis[3-(5-amino-2-hydroxybenzyl)-3H-imidazol-1-ium]butane dichloride monohydrate;

1,3-bis{3-{3'-[(4"-aminoanilino)-N-propyl]}-3H-imidazol-1-ium}propane dichloride;

or an acid addition salt thereof.

12. A method of dyeing keratin fibres comprising applying at least one oxidation base selected from compounds of formula (I) and salts thereof according to claim 1 to said keratin fibres in an amount effective for said dyeing.

13. A method according to claim 12, wherein said keratin fibres are human keratin fibres.

14. A method according to claim 13, wherein said human keratin fibres are human hair.

15. A composition for the oxidation dyeing of keratin fibres, comprising, in a medium suitable for dyeing, at least one oxidation base selected from compounds of formula (I) and acid addition salts thereof according to claim 1.

16. A composition according to claim 15, wherein said at least one oxidation base is present in an amount ranging from about 0.0005 to about 12% by weight relative to the total weight of the dye composition.

17. A composition according to claim 16, herein said at least one oxidation base is present in an amount ranging from 0.005 to 6% by weight relative to the total weight of the dye composition.

18. A composition according to claim 15, wherein said medium suitable for dyeing comprises water or a mixture of water and at least one organic solvent selected from $C_1$–$C_4$ lower alkanols, glycerol, glycols and glycol ethers, and aromatic alcohols.

19. A composition according to claim 18, wherein said at least one organic solvent is selected from ethanol, isopropanol, 2-butoxyethanol, propylene glycol, propylene glycol monomethyl ether, diethylene glycol monoethyl ether, monomethyl ether, benzyl alcohol and phenoxyethanol.

20. A composition according to claim 19, wherein said at least one organic solvent is present in amount ranging from 1 to 40% by weight relative to the total weight of the composition.

21. A composition according to claim 20, wherein said at least one organic solvent is present in amount ranging from 5 to 30% by weight relative to the total weight of the composition.

22. A composition according to claim 15, having a pH ranging from 3 to 12.

23. A composition according to claim 22, having a pH ranging from 5 to 11.

24. A composition according to claim 15, wherein said composition further comprises at least one additional oxidation base selected from para-phenylenediamines, bis (phenyl)alkylenediamines other than the compound of formula (I), para-aminophenols, ortho-aminophenols and heterocyclic bases other than the compound of formula (I).

25. A composition according to claim 24, wherein said at least one additional oxidation base is selected from para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(4'-hydroxyethyl)-N,N'-bis(4-aminophenyl)tetramethylenediamine, N,N'-bis(4-methylaminophenyl)tetramethylenediamine and N,N '-bis(ethyl)-N,N'-bis(4'-amino-3'-methylphenyl) ethylenediamine, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, 2-aminophenol, 2-amino-5-methylphenol, 2-amino-6-methylphenol, 5-acetamido-2-aminophenol, pyridine derivatives, pyrimidine derivatives and pyrazole derivatives.

26. A composition according to claim 24, wherein said at least one additional oxidation base is present in an amount ranging from 0.0005 to 12% by weight relative to the total weight of the dye composition.

27. A composition according to claim 26, wherein said at least one additional oxidation base is present in an amount ranging from 0.005 to 6% by weight relative to the total weight of the dye composition.

28. A composition according to claim 15, wherein said composition further comprises at least one coupler and/or at least one direct dye.

29. A composition according to claim 28, wherein said at least one coupler is selected from meta-phenylenediamines, meta-aminophenols, meta-diphenols and heterocyclic couplers, and acid addition salts thereof.

30. A composition according to claim 29, wherein said at least one coupler is selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and acid addition salts thereof.

31. A composition according to claim 28, wherein said at least one coupler is present in an amount ranging from 0.0001 to 10% by weight relative to the total weight of the dye composition.

32. A composition according to claim 31, wherein said at least one coupler is present in an amount ranging from 0.005 to 5% by weight relative to the total weight of the dye composition.

33. A composition according to claim 15, wherein said acid addition salt are selected from the hydrochlorides, hydrobromides, sulphates, citrates, succinates, tartrates, lactates and acetates.

34. A process for dyeing keratin fibres, comprising the steps of:
    applying at least one dye composition according to claim 15 to said keratin fibres, and
    developing a colour at acidic, neutral or alkaline pH with an oxidizing agent, said oxidizing agent being added to the dye composition at the time of applying to said fibres or being present in an oxidizing composition which is applied simultaneously or sequentially with said dye composition.

35. A process according to claim 34, wherein said oxidizing agent is selected from hydrogen peroxide, urea peroxide, alkali metal bromates and persalts.

36. A process according to claim 36, wherein said oxidizing agent is selected from perborates and persulphates.

37. A process according to claim 35, wherein said oxidizing agent is hydrogen peroxide.

38. A multi-compartment dyeing device or kit for dyeing keratin fibres comprising at least two compartments, wherein
    a first compartment comprises a dye composition according to claim 15, and
    a second compartment comprises an oxidizing composition.

39. A composition according to claim 16, wherein said composition is in the form of a liquid, a cream, or a gel.

* * * * *

UNITED STATES PATENT AND TRADEMARK OFFICE
CERTIFICATE OF CORRECTION

PATENT NO.   : 6,270,533 B1
DATED        : August 7, 2001
INVENTOR(S)  : Alain Genet et al.

It is certified that error appears in the above-identified patent and that said Letters Patent is hereby corrected as shown below:

Column 32,
Line 13, "4-tetramethyidiammonium" should read -- 4-tetramethyldiammonium --.
Line 37, "herein" should read -- wherein --.

Column 34,
Line 17, "acid addition salt are selected" should read -- acid addition salt is selected --.

Signed and Sealed this

Sixth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,270,533 B1                                    Page 1 of 1
DATED         : August 7, 2001
INVENTOR(S)   : Alain Genet et al.

It is certified that error appears in the above-identified patent and that said Letters Patent is hereby corrected as shown below:

<u>Column 33,</u>
Line 14, "(4'-hydroxyethyl)" should read -- (ß-hydroxyethyl) --.

Signed and Sealed this

Twenty-fourth Day of December, 2002

JAMES E. ROGAN
*Director of the United States Patent and Trademark Office*